(12) United States Patent
Park et al.

(10) Patent No.: US 10,234,408 B2
(45) Date of Patent: Mar. 19, 2019

(54) METHOD FOR ANALYZING THE LENGTH OF SULFUR CROSSLINKING BONDS IN A VULCANIZED RUBBER

(71) Applicant: LG Chem, Ltd., Seoul (KR)

(72) Inventors: Hee Yong Park, Daejeon (KR); Yu Ra Lee, Daejeon (KR); Hye Sung Cho, Daejeon (KR)

(73) Assignee: LG Chem, Ltd. (KR)

( * ) Notice: Subject to any disclaimer, the term of this patent is extended or adjusted under 35 U.S.C. 154(b) by 113 days.

(21) Appl. No.: 15/468,507

(22) Filed: Mar. 24, 2017

(65) Prior Publication Data

US 2017/0315071 A1    Nov. 2, 2017

(30) Foreign Application Priority Data

May 2, 2016 (KR) ............... 10-2016-0054144

(51) Int. Cl.
*G01N 24/08* (2006.01)
(52) U.S. Cl.
CPC .................. *G01N 24/087* (2013.01)
(58) Field of Classification Search
CPC .................................................. G01N 24/087
See application file for complete search history.

(56) References Cited

U.S. PATENT DOCUMENTS

| 7,497,129 B2 * | 3/2009 | Kimura | .................. G01N 24/08 73/842 |
| 7,804,298 B2 | 9/2010 | Miura et al. | |

(Continued)

FOREIGN PATENT DOCUMENTS

| JP | 2002071595 A | 3/2002 |
| JP | 2006317414 A | 11/2006 |

(Continued)

OTHER PUBLICATIONS

Chae, Young Kee, et al., "A simple NMR method to measure crosslink density of natural rubber composite." Polymer Testing, vol. 29, 2010, pp. 953.957.

(Continued)

*Primary Examiner* — Rodney A Bonnette
(74) *Attorney, Agent, or Firm* — Lerner, David, Littenberg, Krumholz & Mentlik, LLP

(57) ABSTRACT

The present invention relates to a method for analyzing the length of sulfur crosslinking bonds in a vulcanized rubber using NMR spectrum. In some embodiments, the method comprises obtaining, independently, a carbon-13 nuclear magnetic resonance ($^{13}C$ NMR) spectrum of a standard substance, wherein the standard substance containing carbon atoms, and a $^{13}C$ NMR spectrum of the vulcanized rubber, wherein the $^{13}C$ NMR spectrum of the standard substance and the $^{13}C$ NMR spectrum of the vulcanized rubber are obtained under the same conditions; obtaining, independently, free induction decay (FID) amplification values of characteristic peaks in the $^{13}C$ NMR spectrum of the standard substance, and FID amplification values of characteristic peaks in the $^{13}C$ NMR spectrum of the vulcanized rubber; and measuring the length of sulfur crosslinking bonds in the vulcanized rubber.

5 Claims, 3 Drawing Sheets

(56) References Cited

U.S. PATENT DOCUMENTS

| 9,488,707 B2 | 11/2016 | Kobayashi et al. |
| 2009/0033325 A1 | 2/2009 | Miura et al. |
| 2013/0335078 A1 | 12/2013 | Kobayashi et al. |
| 2015/0203693 A1 | 7/2015 | Mestan |

FOREIGN PATENT DOCUMENTS

| JP | 4555294 B2 | 9/2010 |
| JP | 2013257239 A | 12/2013 |
| JP | 2015529712 A | 10/2015 |
| KR | 101214907 B1 | 12/2012 |

OTHER PUBLICATIONS

Chen, Li-Shi et al., "Calibration of solid state NMR carbon structural parameters and application in coal structure analysis", Journal of Fuel Chemistry and Technology, Oct. 2017, vol. 45, No. 10, pp. 1153-1163 (Abstract Only).

Dybowski, C. et al., "Solid-State NMR Spectroscopy", Analytical Chemistry, Jun. 15, 2008, vol. 80, No. 12, pp. 4295-4300.

Xue, Q., "Spectroscopy in research of polymer structure", published on May 1995, No. 1, pp. 263-296, (Partial English Translation).

\* cited by examiner ions METHOD FOR ANALYZING THE LENGTH OF SULFUR CROSSLINKING BONDS IN A VULCANIZED RUBBER

CROSS-REFERENCE TO RELATED APPLICATION

This application claims the benefit of priority from Korean Patent Application No. 10-2016-0054144 filed on May 2, 2016 with the Korean Intellectual Property Office, the disclosure of which is herein incorporated by reference in its entirety.

TECHNICAL FIELD

The present invention relates to a method for analyzing the length of sulfur crosslinking bonds in a vulcanized rubber using NMR spectrum.

BACKGROUND ART

Sulfur crosslinking bonds are introduced in a vulcanized rubber, and mono-, di-, tri-, poly-sulfur linkages and the like are introduced depending on the length of the sulfur crosslinking bonds. The length of such sulfur crosslinking bonds greatly affects the physical/chemical properties of the vulcanized rubber. For example, the shorter the length of the crosslinking bonds, the greater the rigidity of the vulcanized rubber. Therefore, it is very important to analyze the length of sulfur crosslinking bonds in a vulcanized rubber.

However, a method for analyzing the length of sulfur crosslinking bonds in the vulcanized rubber is extremely limited. For example, when analyzed by NMR, it is only possible to analyze mono-sulfur linkages (sulfur crosslinking bonds composed of one sulfur atom) and poly-sulfur crosslinking bonds (sulfur crosslinking bonds composed of two or more sulfur atoms), and it is difficult to analyze an average sulfur length.

In addition to NMR, it is possible to distinguish the types of crosslinking bonds by vulcanization using a solvent method. However, it can only analyze mono-sulfur linkages (sulfur crosslinking bonds composed of one sulfur atom), di-sulfur linkages (sulfur crosslinking bonds composed of two sulfur atoms) and poly-sulfur linkage (sulfur crosslinking bonds composed of three or more sulfur atoms), and it is also difficult to analyze the average sulfur length. In addition, the solvent method must use a toxic solvent and has a long measurement time, which are disadvantages.

As such, the reason why it is difficult to analyze the average sulfur length of sulfur crosslinking bonds in the vulcanized rubber is that the chemical shift between the structures of the di-sulfur linkages (sulfur crosslinking bonds composed of two sulfur atoms) and the poly-sulfur linkages (sulfur crosslinking bonds composed of three or more sulfur atoms) is not so significant, only enabling for the mono-sulfur linkages of the poly-sulfur linkages to be distinguished. Also, in the case of the poly-sulfur linkages, it is difficult to confirm how many sulfur atoms participate in the crosslinking.

On the other hand, since the integrated intensity of a signal in an NMR spectrum is proportional to the nuclear species appearing in the corresponding signal, quantification can be performed based on the specific signal of the compound to be quantified. That is, if a standard substance that knows its molecular structure is added together to a sample for an accurate quantitative analysis, the integrated intensity of a signal of a standard substance in a NMR spectrum, and the integrated intensity of a specific signal of a compound to be quantified can be obtained. In this case, since the molecular structure and the amount of the standard substance are known, quantitative analysis of a compound in the sample is possible. The standard substance that is added together with the sample is referred to as an 'internal standard'.

However, the quantitative analysis described above has a problem that it is difficult to apply to an insoluble sample, particularly to the vulcanized rubber which is the target for analysis of the present invention. The most important reason is that in order to obtain a significant NMR spectrum, the sample and the standard substance should be uniformly mixed, but in the case of the insoluble sample, the sample is not mixed in a solvent and therefore, it is difficult to uniformly mix the sample.

In this regard, in the present invention, in order to analyze the length of the sulfur crosslinking bonds in the vulcanized rubber, the NMR spectra of the standard substance and the vulcanized rubber are separately obtained and analyzed, rather than mixing the standard substance with the vulcanized rubber, and the standard substance used herein is referred to as an 'external standard'. Further, the length of sulfur crosslinking bonds in the vulcanized rubber was analyzed by extracting useful information from each NMR spectrum.

DETAILED DESCRIPTION OF THE INVENTION

Technical Problem

One object of the present invention is to provide a method for analyzing the length of sulfur crosslinking bonds in a vulcanized rubber using NMR spectrum.

Technical Solution

To achieve the above object, the present invention provides a method for analyzing the length of sulfur crosslinking bonds in a vulcanized robber comprising the steps of:
1) obtaining independently a $^{13}C$ NMR spectrum of a standard substance containing carbon atoms, and a $^{13}C$ NMR spectrum of the vulcanized rubber under the same condition;
2) obtaining independently FID (free induction decay) amplification values of characteristic peaks in the NMR spectrum of the standard substance and in the NMR spectrum of the vulcanized rubber; and
3) measuring the length of sulfur crosslinking bonds in the vulcanized rubber according to the following Equation:

$$\text{Length of sulfur crosslinking bonds in the vulcanized rubber} = 2 \times (A/B) \times (C/(D \times E)) \quad \text{[Equation 1]}$$

In the equation 1 above,
A is the number of moles of sulfur atoms in the vulcanized rubber used to obtain the NMR spectrum of the vulcanized rubber,
B is the FID amplification value of the vulcanized rubber,
C is the FID amplification value of the standard substance,
D is the number of atoms corresponding to the characteristic peak of the standard substance in a molecule of the standard substance, and
E is the number of moles of the standard substance used to obtain the NMR spectrum of the standard substance.

The present invention relates to a method for analyzing the length of sulfur crosslinking bonds in a sulfur crosslink present in a vulcanized rubber, and is characterized in that it is analyzed using NMR spectrum. Sulfur crosslinking bonds are introduced in a vulcanized rubber, and mono-, di-, tri-, poly-sulfur linkages and the like are introduced depending on the length of the sulfur crosslinking bonds. The length of such sulfur crosslinking bonds greatly affects the physical/chemical properties of the vulcanized rubber, and therefore, it is very important to analyze the length of sulfur crosslinking bonds in the vulcanized rubber.

However, a method for analyzing the length of sulfur crosslinking bonds in a vulcanized rubber is extremely limited, and this is because the signal difference according to the length of sulfur crosslinking bonds is not significant during a NMR analysis, rendering the analysis difficult. Accordingly, until now, the analysis of sulfur crosslinking bonds in the vulcanized rubber is limited to the analysis of mono-, di- and poly-sulfur linkages, which can analyze signal differences, and this is not only a partial analysis, but also is less accurate, and thus it was difficult to analyze the length of sulfur crosslinking bonds in the entire vulcanized rubber.

On the other hand, since the integrated intensity of a signal in an NMR spectrum is proportional to the nuclear species appearing in the corresponding signal, quantification can be performed based on the specific signal of the compound to be quantified. That is, when a standard substance that knows its molecular structure is added together to a sample for an accurate quantitative analysis, the integrated intensity of a signal of a standard substance in a NMR spectrum and the specific signal intensity of the compound to be quantified can be obtained. In this case, since the molecular structure and the amount of the standard substance are known, quantitative analysis of a compound in the sample is possible. Thus, the standard substance that is added together with the sample is referred to as an 'internal standard'.

However, the quantitative analysis as described above has a problem that it is difficult to apply to an insoluble sample, particularly to the vulcanized rubber which is the target for analysis of the present invention. The most important reason is that in order to obtain a significant NMR spectrum, the sample and the standard substance should be uniformly mixed, but in the case of the insoluble sample, the sample is not mixed in a solvent and therefore, it is difficult to uniformly mix the sample.

In the present invention, in order to analyze the length of the sulfur crosslinking bonds in the vulcanized rubber, the NMR spectra of the standard substance and the vulcanized rubber are separately obtained and analyzed, rather than mixing the standard substance with the vulcanized rubber, and the standard substance used herein is referred to as an 'external standard'. Further, the length of sulfur crosslinking bonds in the vulcanized rubber was analyzed by extracting useful information from each NMR spectrum.

Herein below, the present invention will be described in detail for each step.

Step 1 of the present invention is a step of obtaining the NMR spectra of the standard substance and the vulcanized rubber, respectively.

Because of obtaining the respective NMR spectra and comparing them, the $^{13}$C NMR spectrum is obtained by using carbon atoms of the vulcanized rubber as NMR active atoms.

In addition, since a quantitative analysis is carried out by obtaining the NMR spectra of the standard substance and the vulcanized rubber and comparing them, the conditions for obtaining the NMR spectrum should be the same. The above condition means a condition necessary for NMR measurement, and for example, it means that, when performing NMR measurement, the number of scans, the delay time, the pulse width, the pulse power, the receiver gain, and the spinning rate are the same. Further, the scope of each condition is not limited, as long as it is suitable for obtaining the respective NMR spectra under the same condition.

On the other hand, in the case of the standard substance, since the molecular structure, molecular weight and mass thereof used for obtaining the NMR spectra can be known, quantitative analysis can be performed while utilizing them later. Further, in the case of the standard substance, its type is not particularly limited as long as a characteristic peak appears in the NMR spectrum, and preferably, a substance in which a characteristic peak prominently appears in the NMR spectrum is used. For example, hexamethylbenzene (HMB) is preferable.

Step 2 of the present invention is a step of obtaining FID amplification values of the characteristic peaks in each of the NMR spectra obtained in Step 1 above.

The NMR spectrum is based on the free induction decay (FID), which is an electrical signal observed in a magnetic field, and it is converted into a spectrum because the FID itself is difficult to be analyzed. During the process, a phase adjustment, a baseline correction and a peak integration are performed. In the NMR spectrum, the integrated intensity of a specific peak is directly proportional to the number of nuclei appearing at the peak, and so this can be used for quantitative analysis. However, when many peaks overlap in the NMR spectrum, it is difficult to obtain the integral intensity, and thus it is difficult to carry out quantitative analysis.

However, conversely, the FID can be extracted at a specific peak region of the NMR spectrum. In this case, the FID amplification values can be extracted. These FID amplification values contain quantitative information on specific peaks in the NMR spectrum, thus enabling the quantitative analysis by the extraction thereof. The FID amplification value can be obtained, for example, using Agilent's Vnmrj 4.2 software.

That is, the FID amplification value in a specific peak region of the NMR spectrum of the standard substance is directly proportional to the amount of the nuclide appearing at the corresponding peak, and the NMR spectrum of the sample is obtained under the same condition as the NMR spectrum of the standard substance, and the above proportional relationship can be applied even to the FID amplification value of the sample. Therefore, if the FID amplification value is obtained on the basis of the specific peak of the compound to be quantified from the NMR spectrum of the sample, it is possible to quantitatively analyze the compound by comparing it with the FID amplification value of the standard substance.

Step 3 of the present invention is a step of analyzing the concentration of the compound in the sample from each of the FID amplification value obtained in Step 2 above.

In Step 2 above, if the FID amplification values of the characteristic peaks are obtained in the NMR spectrum of the standard substance, the molecular structure of the standard substance and the used amount thereof are known, and thus a quantitative analysis can be performed based on the values thereof.

For example, when the $^{13}$C NMR spectrum is obtained using HMB as a standard substance, the characteristic peak of a methyl group (—CH$_3$) of HMB appears. When the FID amplification value for the methyl group peak is obtained, a value proportional to the amount of the standard substance used can be obtained. Based on the FID amplification values derived therefrom, it can be used for the analysis of the FID amplification values obtained from the $^{13}$C NMR spectrum of the vulcanized rubber.

On the other hand, as shown in FIG. 1, carbon atoms crosslinked with sulfur atoms are present in the sulfur crosslinking bonds in the vulcanized rubber, and these carbon atoms become a crosslinking point of the sulfur crosslinking bond. When the $^{13}$C NMR spectrum of the vulcanized rubber is obtained, the peak corresponding to such a crosslinking point appears as a characteristic peak, and an FID amplification value can be obtained based on the peak thereof. Therefore, by comparing the obtained FID amplification values and the FID amplification values of the standard substance, the number of crosslinking points present in the vulcanized rubber can be derived.

Further, the content of the sulfur atoms present in the vulcanized rubber can be obtained by an IC analysis. Therefore, under the assumption that there is no dangling chain in the vulcanized rubber, it is possible to obtain the number of crosslinking points present in the vulcanized rubber and the number of sulfur elements present in the vulcanized rubber. From this, the average length of the sulfur crosslinking bonds in the vulcanized rubber can be analyzed.

Specifically, the average length of the sulfur crosslinking bonds in the vulcanized rubber can be analyzed as shown in Equation 1 below:

$$\text{Length of sulfur crosslinking bonds in the vulcanized rubber} = 2 \times (A/B) \times (C/(D \times E)) \quad [\text{Equation 1}]$$

In the equation 1 above,

A is the number of moles of sulfur atoms in the vulcanized rubber used to obtain the NMR spectrum of the vulcanized rubber, B is the FID amplification value of the vulcanized rubber, C is the FID amplification value of the standard substance, D is the number of atoms corresponding to the characteristic peak of the standard substance in a molecule of the standard substance, and E is the number of moles of the standard substance used to obtain the NMR spectrum of the standard substance.

In the equation 1, A is the number of moles of sulfur atoms in the vulcanized rubber used to obtain the NMR spectrum of the vulcanized rubber, which can be confirmed by the IC analysis. B and C are the values that can be obtained through steps 1 and 2 described above. D is the number of atoms corresponding to the characteristic peak of the standard substance in a molecule of the standard substance. For example, when HMB is used as a standard substance and the characteristic peak is a methyl group, the number of methyl groups in the HMB molecule is 6, and thus, the value of D is 6. E, which is the number of moles of the standard substance, refers the number of moles used to obtain the NMR spectrum. Further, the reason for multiplying 2 in the equation 1 above is that the sulfur crosslinking bonds must have two crosslinking points.

A specific example in which the equation 1 is applied will be further described in the following embodiments.

Furthermore, the number of moles of the crosslinking points per gram of the vulcanized rubber can be analyzed by modifying the equation 1 above, and is specifically analyzed as shown in Equation 2 below:

$$\text{Number of moles of crosslinking points per gram of the vulcanized rubber (mol/g)} = B \times ((D \times E)/C)/F \quad [\text{Equation 2}]$$

In the equation 2 above,

B is the FID amplification value of the vulcanized rubber,

C is the FID amplification value of the standard substance,

D is the number of atoms corresponding to the characteristic peak of the standard substance in a molecule of the standard substance, E is the number of moles of the standard substance used to obtain the NMR spectrum of the standard substance, and F is the mass of the vulcanized rubber used to obtain the NMR spectrum of the vulcanized rubber.

As described above, the present invention is characterized in that the NMR spectra are obtained by the method of using the external standard, and that the length of the sulfur crosslinking bonds in vulcanized rubber can be analyzed from the information thereof.

Advantageous Effect

The present invention is characterized in that the quantitative analysis is performed by a method of using an external standard which obtains NMR spectra of a sample and a standard substance and then compares them, thereby enabling the analysis of the length of the sulfur crosslinking bonds in the vulcanized rubber which could not be measured in the prior art.

DETAILED DESCRIPTION OF THE EMBODIMENTS

Hereinafter, preferred examples will be presented to aid in understanding of the present invention. However, the following examples are provided for illustrative purposes only, and the content of the present invention is not limited by these Examples.

In the following examples, Agilent INOVA 400 MHz SSNMR (using T3 SSNMR probe) was used for NMR spectrum, and Agilent's Vnmrj 4.2 software was used to measure the FID amplitudes values.

PREPARATION EXAMPLE

Preparation of Samples

A rubber having a weight ratio between NR/SBR/BR of 10:58:32 was prepared, and 2 types of vulcanized rubbers were prepared by a vulcanization reaction in which the content of sulfur added was varied. The sulfur contents of each vulcanized rubber were measured by IC analysis and found to be 1.22 wt % and 1.20 wt %, respectively, and these were used as the first and second samples below.

Example 1

A $^{13}$C SSNMR spectrum for 49.4 mg of hexamethylbenzene (HMB) was obtained as an external standard under the following conditions.

pulse power(tpwr)=61
pulse width(pw)=90 degree pulse (3.00 usec)
ax90=3800
delay time=10 sec number of scans=15000 receiver gain=60 spinning rate=3 kHz

Temperature=80° C.

The FID amplification value was obtained for the peak corresponding to the methyl group of HMB in the obtained $^{13}$C SSNMR spectrum, and the result thereof is shown in Table 1 below.

Subsequently, a $^{13}$C SSNMR spectrum for 54.9 mg of the first sample was obtained under the same conditions as above. In the NMR spectrum thereof, the FID amplification value for the characteristic peak of alpha-methine, which is a crosslinking point, was extracted, and the result is shown in Table 1 below.

The measured results were calculated as shown in Table 1, and the average length of sulfur crosslinking bonds the first sample was analyzed.

TABLE 1

| | |
|---|---|
| Mass of the first sample | 54.9 mg |
| Sulfur content in the first sample | 1.22 wt % |
| (A) # of moles of sulfur atoms in the first sample | 2.09 × 10$^{-5}$ mol |
| (B) FID amplification value of the first sample | 6.09612 |
| Mass of HMB | 49.4 mg |
| Molecular weight of HMB | 162.14 g/mol |
| (C) FID amplification value of HMB | 2770.08 |
| (D) # of methyl groups in HMB | 6 |
| (E) # of moles of HMB | 0.000305 mol | of moles of crosslinking points in the first sample = B × ((D × E)/C)/(54.9 mg) = 7.33 × 10$^{-5}$ mol/g
Average length of sulfur crosslinking bonds in the first sample = 2 × (A/B) × (C/(D × E)) = 10.4

Example 2

Figure 1:
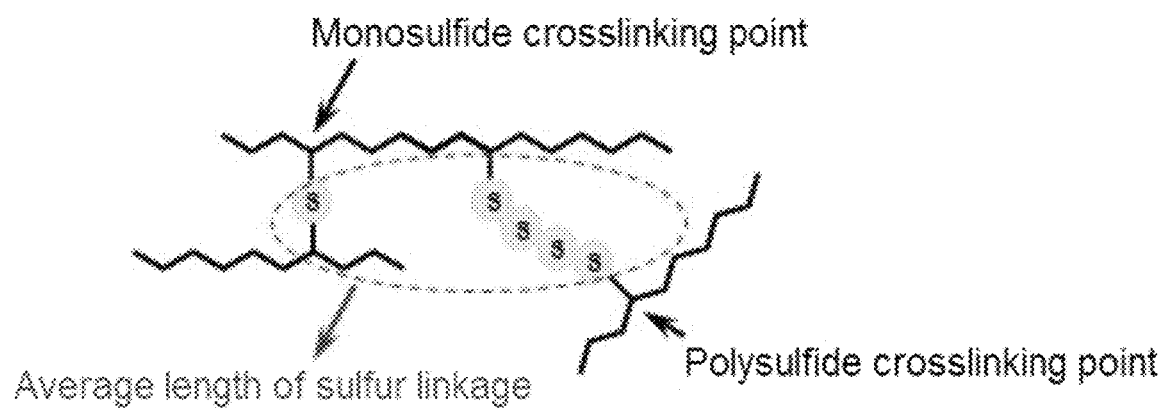
FIG. 1 schematically shows the types of sulfur crosslinking bonds in the vulcanized rubber in the present invention.
Figure 2:
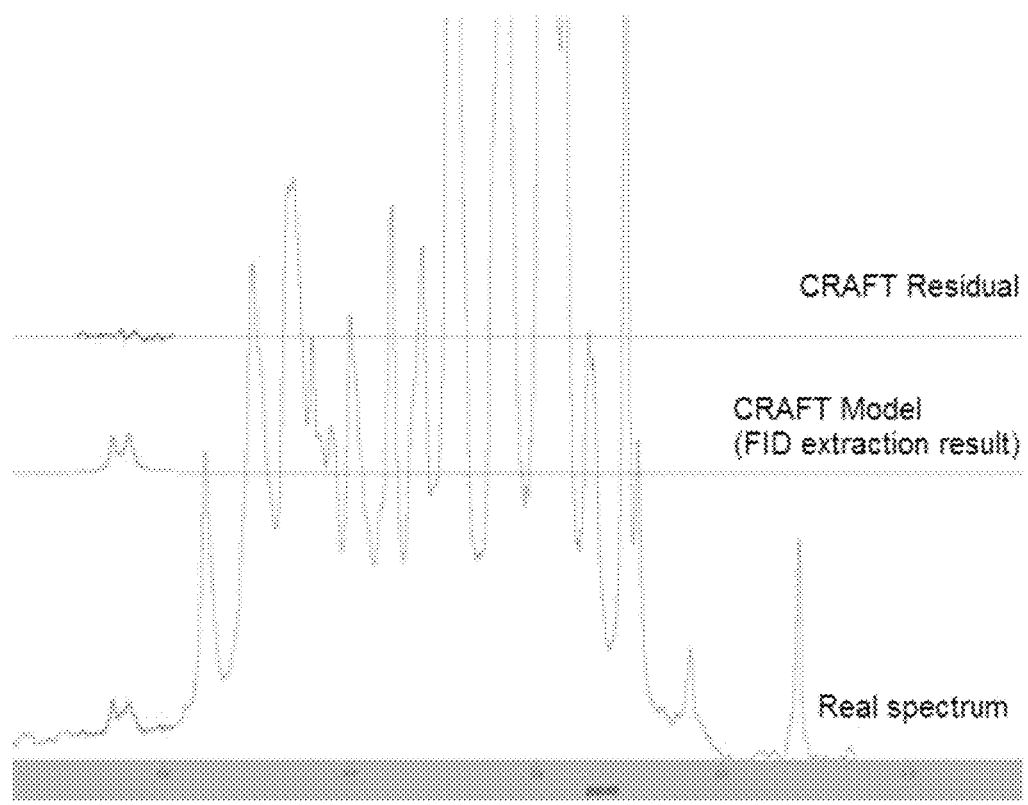
FIG. 2 shows the extraction result of the FID amplification values for the second sample in the example of the present invention.

A $^{13}$C SSNMR spectrum for 56.7 mg of the second sample was obtained under the same conditions as in Example 1. In the NMR spectrum thereof, the FID amplification value for the characteristic peak of alpha-methine, which is a crosslinking point, was extracted, and the result is shown in FIG. 2 and Table 2 below. As for the FID amplification value for the standard substance, the value previously obtained in Example 1 was used.

The measured results were calculated as shown in Table 2, and the average length of sulfur crosslinking bonds in the second sample was analyzed.

TABLE 2

| | |
|---|---|
| Mass of the second sample | 56.7 mg |
| Sulfur content in the second sample | 1.20 wt % |
| (A) # of moles of sulfur atoms in the second sample | 2.13 × 10$^{-5}$ mol |
| (B) FID amplification value of the second sample | 5.06992 |
| Mass of HMB | 49.4 mg |
| Molecular weight of HMB | 162.14 g/mol |
| (C) FID amplification value of HMB | 2770.08 |
| (D) # of methyl groups in HMB | 6 |
| (E) # of moles of HMB | 0.000305 mol |

Number of moles of crosslinking points in the second sample = B × ((D × E)/C)/(56.7 mg) = 5.90 × 10$^{-5}$ mol/g
Average length of sulfur crosslinking bonds in the second sample = 2 × (A/B) × (C/(D × E)) = 12.7

Experimental Example

In order to verify the results obtained in Examples 1 and 2 above, the verification was conducted by the method described in the literature (Polymer Testing 29 (2010) 953-957).

The literature relates to a method of estimating the cavity size by using toluene as a probe and measuring the degree of a chemical shift of toluene trapped in a cavity of natural rubber. The trapped toluene has a smaller difference in the chemical shift with untrapped toluene as the cavity size in natural rubber increases. Conversely, the smaller the cavity size in natural rubber, the greater the difference in the chemical shift with the untrapped toluene.

Figure 3:
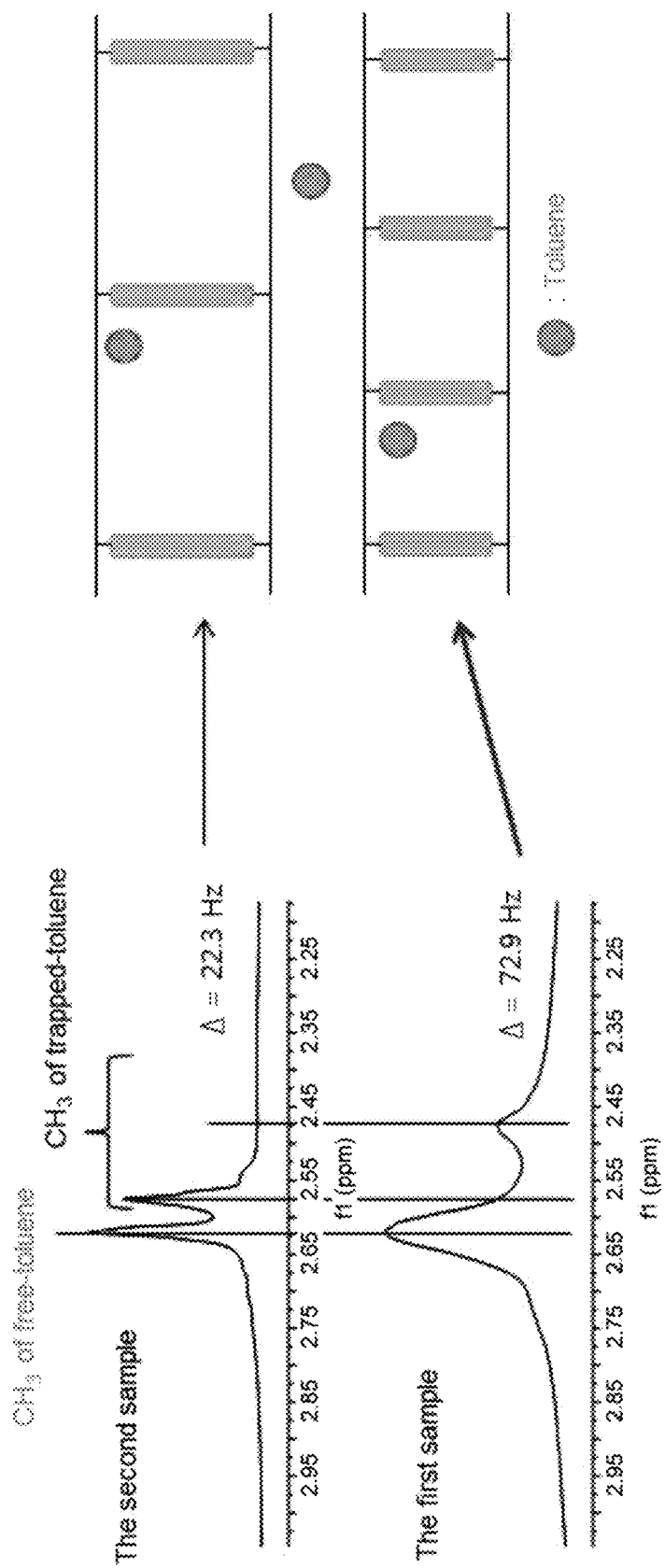
FIG. 3 shows NMR spectra measured to verify the results analyzed in the examples of the present invention.

The number of moles of the crosslinking points and the average length of the sulfur crosslinking bonds in the first and second samples used in Examples 1 and 2 can correspond to the cavity size signified in the literature above. Accordingly, the NMR spectra were obtained according to the method described in the literature above, and the results are shown in FIG. 3. As shown in FIG. 3, the difference in the chemical shift of the second sample was smaller than that of the first sample, suggesting that the cavity size of the second sample is larger than that of the first sample. These results are consistent with the results showing that the number of moles of cross-linking points of the second sample is relatively smaller than that of the first sample and that the average length of sulfur crosslinking bonds in the second sample is relatively larger than that of the first sample measured in the previous examples.

The invention claimed is:

1. A method of analyzing the length of sulfur crosslinking bonds in a vulcanized rubber, comprising:
    1) obtaining, independently, a carbon-13 nuclear magnetic resonance ($^{13}$C NMR) spectrum of a standard substance, wherein the standard substance contains carbon atoms, and a $^{13}$C NMR spectrum of the vulcanized rubber, wherein the $^{13}$C NMR spectrum of the standard substance and the $^{13}$C NMR spectrum of the vulcanized rubber are obtained under the same conditions;
    2) obtaining, independently, free induction decay (FID) amplification values of characteristic peaks in the $^{13}$C NMR spectrum of the standard substance, and FID amplification values of characteristic peaks in the $^{13}$C NMR spectrum of the vulcanized rubber; and
    3) measuring the length of sulfur crosslinking bonds in the vulcanized rubber according to the following Equation:

$$\text{Length of sulfur crosslinking bonds in the vulcanized rubber} = 2 \times (A/B) \times (C/(D \times E)) \quad \text{[Equation 1]}$$

wherein,
A is the number of moles of sulfur atoms in the vulcanized rubber used to obtain the $^{13}$C NMR spectrum of the vulcanized rubber,
B is the FID amplification value of a characteristic peak in the $^{13}$C NMR spectrum of the vulcanized rubber,
C is the FID amplification value of a characteristic peak in the $^{13}$C NMR spectrum of the standard substance,
D is the number of atoms corresponding to the characteristic peak in the $^{13}$C NMR spectrum of the standard substance in a molecule of the standard substance, and
E is the number of moles of the standard substance used to obtain the $^{13}$C NMR spectrum of the standard substance.

2. The analysis method according to claim 1,
wherein the $^{13}$C NMR spectrum of the standard substance and the $^{13}$C NMR spectrum of the vulcanized rubber in step 1) are obtained using the same number of scans, delay time, pulse width, pulse power, receiver gain, spinning rate, and temperature.

3. The analysis method according to claim 1,
wherein the standard substance is hexamethylbenzene.

4. The analysis method of claim 3,
wherein the characteristic peak in the $^{13}$C NMR spectrum of the standard substance is a peak of methyl group.

5. The analysis method according to claim 1,
further comprising:
measuring the number of moles of crosslinking points per gram of the vulcanized rubber according to the following Equation 2:

$$\text{Number of moles of crosslinking points per gram of the vulcanized rubber (mol/g)} = B \times ((D \times E)/C)/F \quad \text{[Equation 2]}$$

wherein,
B through E have the same values as described for Equation 1, and
F is the mass of the vulcanized rubber used to obtain the $^{13}$C NMR spectrum of the vulcanized rubber.

* * * * *